United States Patent
Katz et al.

(10) Patent No.: US 10,633,459 B2
(45) Date of Patent: *Apr. 28, 2020

(54) POLYALKOXY FATTY COMPOUND

(71) Applicants: Dow Global Technologies LLC, Midland, MI (US); Rohm and Haas Company, Collegeville, PA (US)

(72) Inventors: Joshua S. Katz, Merion Station, PA (US); Yang Song, Farmingham, MA (US); Timothy J. Young, Bay City, MI (US); David J. Brennan, Midland, MI (US); Florin Dan, Midland, MI (US); Yujing Tan, Midland, MI (US); Susan L. Jordan, Doylestown, PA (US)

(73) Assignee: Dow Global Technologies LLC

( * ) Notice: Subject to any disclaimer, the term of this patent is extended or adjusted under 35 U.S.C. 154(b) by 0 days.

This patent is subject to a terminal disclaimer.

(21) Appl. No.: 16/023,049

(22) Filed: Jun. 29, 2018

(65) Prior Publication Data

US 2018/0305467 A1 Oct. 25, 2018

Related U.S. Application Data

(63) Continuation of application No. 15/753,753, filed as application No. PCT/US2016/049850 on Sep. 1, 2016.

(60) Provisional application No. 62/217,136, filed on Sep. 11, 2015.

(51) Int. Cl.
| | | |
|---|---|---|
| *C07K 17/08* | (2006.01) | |
| *C08G 65/332* | (2006.01) | |
| *C08L 71/02* | (2006.01) | |
| *A61K 9/00* | (2006.01) | |
| *A61K 47/10* | (2017.01) | |
| *A61K 47/26* | (2006.01) | |
| *A61K 9/08* | (2006.01) | |
| *A61K 47/34* | (2017.01) | |
| *C08K 5/101* | (2006.01) | |
| *A61K 38/00* | (2006.01) | |
| *C07K 14/475* | (2006.01) | |
| *C07K 14/575* | (2006.01) | |

(52) U.S. Cl.
CPC ............ *C07K 17/08* (2013.01); *A61K 9/0019* (2013.01); *A61K 9/08* (2013.01); *A61K 47/10* (2013.01); *A61K 47/26* (2013.01); *A61K 47/34* (2013.01); *C08G 65/3322* (2013.01); *C08K 5/101* (2013.01); *C08L 71/02* (2013.01); *A61K 38/00* (2013.01); *C07K 14/475* (2013.01); *C07K 14/575* (2013.01); *C08G 2650/50* (2013.01); *C08G 2650/58* (2013.01); *C08L 2203/02* (2013.01)

(58) Field of Classification Search
CPC .... C07K 17/08; C07K 14/475; C07K 14/575; C08K 5/101; C08L 71/02; C08L 2203/02; C08G 65/3322; C08G 2650/50; C08G 2650/58; A61K 9/0019; A61K 9/08; A61K 47/34; A61K 47/10; A61K 47/26; A61K 38/00

See application file for complete search history.

(56) References Cited

U.S. PATENT DOCUMENTS

| | | | |
|---|---|---|---|
| 2,183,853 | A | 12/1939 | Haussmann et al. |
| 4,165,405 | A | 8/1979 | Login et al. |
| 5,635,461 | A | 6/1997 | Onitsuka et al. |
| 5,766,612 | A | 6/1998 | Strecker et al. |
| 6,146,622 | A | 11/2000 | Castillo et al. |
| 6,387,359 | B1 | 5/2002 | Ishii et al. |
| 8,226,949 | B2 | 7/2012 | Maggio |
| 8,772,231 | B2 | 7/2014 | Maggio |
| 8,846,044 | B2 | 9/2014 | Maggio |

(Continued)

FOREIGN PATENT DOCUMENTS

| | | |
|---|---|---|
| CN | 102058489 A | 5/2011 |
| EP | 1475100 A1 | 11/2004 |

(Continued)

OTHER PUBLICATIONS

Huntsman, The Jeffamine® Polyetheramines, 2007, p. 1-6.*
May, A., et al.; Langmuir, 2012, p. 9816-9824.*

*Primary Examiner* — Robert S Jones

(57) ABSTRACT

Provided is a composition comprising one or more protein and one or more polyalkoxy fatty compound and wherein said polyalkoxy fatty compound has structure (I)

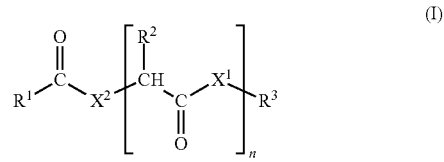

wherein $R^1$ is a fatty group; $R^2$ is H or a substituted or unsubstituted hydrocarbyl group; n is 0 to 5; $X^1$ is O, S, or NH; $X^2$ is O, S, or NH; and $R^3$ is a polymeric group comprising polymerized units of (II) and (III)

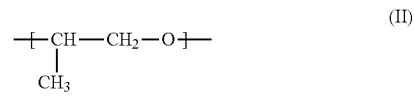

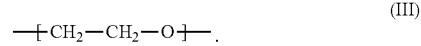

22 Claims, No Drawings

(56) References Cited

U.S. PATENT DOCUMENTS

| | | | |
|---|---|---|---|
| 2002/0176903 A1* | 11/2002 | Kuno | A61K 8/0212 |
| | | | 424/777 |
| 2003/0026818 A1* | 2/2003 | Hoshino | A61K 8/42 |
| | | | 424/401 |
| 2004/0028643 A1* | 2/2004 | Chiba | A61K 8/97 |
| | | | 424/74 |
| 2004/0029829 A1* | 2/2004 | Miyazaki | A61K 8/0212 |
| | | | 514/54 |
| 2007/0243144 A1* | 10/2007 | Takagaki | A61K 8/97 |
| | | | 424/59 |
| 2008/0167215 A1 | 7/2008 | Bittner et al. | |
| 2009/0041848 A1* | 2/2009 | Aimi | A61K 8/64 |
| | | | 424/489 |
| 2013/0029899 A1 | 1/2013 | Hermanson et al. | |
| 2013/0216541 A1 | 8/2013 | Dali et al. | |
| 2015/0007192 A1 | 1/2015 | Lee et al. | |
| 2015/0071879 A1 | 3/2015 | Jezek | |
| 2015/0166616 A1* | 6/2015 | Bancel | C07K 14/47 |
| | | | 514/44 R |

FOREIGN PATENT DOCUMENTS

| | | |
|---|---|---|
| EP | 2301645 A1 | 3/2011 |
| GB | 2311533 A | 10/1997 |
| JP | 50105580 | 8/1975 |
| NO | 3172691 A2 | 10/2001 |
| NO | 2007003936 A1 | 1/2007 |
| NO | 2007135425 A1 | 11/2007 |
| NO | 20090065126 A2 | 5/2009 |
| NO | 2012008779 A2 | 1/2012 |
| NO | 2012028435 A1 | 3/2012 |

* cited by examiner

POLYALKOXY FATTY COMPOUND

It is often desired to provide an aqueous solution of a protein. It is desired that such aqueous solutions remain stable for a long time. Lack of stability includes, for example, either or both of the following processes: denaturing of the protein or agglomeration of the protein molecules.

U.S. Pat. No. 5,635,461 describes an anionic surfactant having the formula

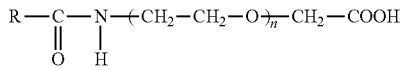

It is desired to provide a surfactant that provides improved stability to an aqueous solution of protein. It is also desired to provide a mixture of such a surfactant with a protein, where the mixture can form an aqueous solution of the protein, where the solution has good stability.

The following is a statement of the invention.

A first aspect of the present invention is a polyalkoxy fatty compound having the structure (I)

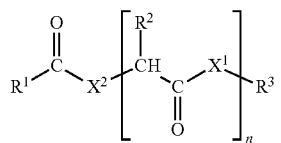

wherein $R^1$ is a fatty group; $R^2$ is H or a substituted or unsubstituted hydrocarbyl group; n is 0 to 5; $X^1$ is S or NH; $X^2$ is O, S, or NH; and $R^3$ is a polymeric group comprising polymerized units of structure (II) and structure (III)

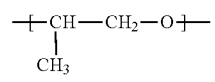

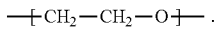

If n is 2 or greater, the various $X_1$ groups may be different from each other or the same as each other, or any combination thereof. If n is 2 or greater, the various $R^2$ groups may be different from each other or the same as each other, or any combination thereof.

A second aspect of the present invention is a composition comprising one or more protein and one or more polyalkoxy fatty compound, wherein the weight ratio of said protein to said polyalkoxy fatty compound is from 0.05:1 to 200:1, and wherein said polyalkoxy fatty compound has structure (I)

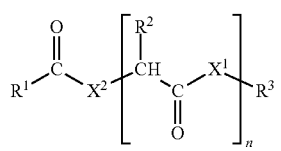

wherein $R^1$ is a fatty group; $R^2$ is H or a substituted or unsubstituted hydrocarbyl group; n is 0 to 5; $X^1$ is O, S, or NH; $X^2$ is O, S, or NH; and $R^3$ is a polymeric group comprising polymerized units of (II) and (III)

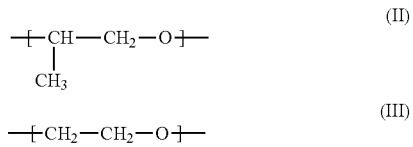

The following is a detailed description of the invention.

As used herein, the following terms have the designated definitions, unless the context clearly indicates otherwise.

A polyalkoxy compound is a compound that contains one or more group having the structure $-(-A-O)_m-$, where m is three or more, and A is an unsubstituted alkyl group. The group A may be linear, branched, cyclic, or a combination thereof. The various A groups among the various $-(-A-O)-$ groups may be the same as each other or different.

A fatty compound is a compound that contains one or more fatty group. A fatty group is a group that contains 8 or more carbon atoms, each of which is bonded to one or more of the other carbon atoms in the group. A polyalkoxy fatty compound is a compound that is both a polyalkoxy compound and a fatty compound.

A hydrocarbyl group is a group that contains hydrogen and carbon atoms. An unsubstituted hydrocarbyl group contains only hydrogen and carbon atoms. A substituted hydrocarbyl group contains one or more substituent group that contains one or more atom other than hydrogen and carbon.

A polymeric group is a relatively large group made up of the reaction products of smaller chemical repeat units. Polymeric groups have number-average molecular weight of 500 or more. Polymeric groups may have structures that are linear, branched, star shaped, looped, hyperbranched, cross-linked, or a combination thereof; polymeric groups may have a single type of repeat unit ("homopolymeric groups") or they may have more than one type of repeat unit ("copolymeric groups"). Copolymeric groups may have the various types of repeat units arranged randomly, in sequence, in blocks, in other arrangements, or in any mixture or combination thereof.

Molecules that can react with each other to form the repeat units of a polymeric group are known herein as "monomers." The repeat units so formed are known herein as "polymerized units" of the monomer. A compound containing one or more polymeric group is a polymer.

A protein is a polymer in which the polymerized units are polymerized units of amino acids. The amino acids are bonded together by peptide bonds. A protein contains 20 or more polymerized units of one or more amino acids. The term protein includes linear polypeptide chains as well as more complex structures that contain polypeptide chains.

A protein is considered to be in solution in a liquid medium (or, synonymously, dissolved in the liquid medium) if the molecules of the protein are distributed throughout the continuous liquid medium in the form of dissolved individual molecules. The protein is considered to be dissolved in water if the continuous liquid medium contains water in the amount of 60% or more by weight based on the weight of the continuous liquid medium.

A chemical group is an ionic group if there is a pH value between 4.5 and 8.5 such that, when the chemical group is in contact with water at that pH value, 50 mole % or more of those chemical groups present are in ionic form.

A buffer is either (i) a compound that has the ability to accept a proton to form the conjugate acid of that compound, and the conjugate acid of that compound has pKa of less than 9, or (ii) a compound that has the ability to release a proton, and the compound has pKa of greater than 5.

When a ratio is said herein to be X:1 or greater, it is meant that the ratio is Y:1, where Y is greater than or equal to X. For example, if a ratio is said to be 3:1 or greater, that ratio may be 3:1 or 5:1 or 100:1 but may not be 2:1. Similarly, when a ratio is said herein to be W:1 or less, it is meant that the ratio is Z:1, where Z is less than or equal to W. For example, if a ratio is said to be 15:1 or less, that ratio may be 15:1 or 10:1 or 0.1:1 but may not be 20:1.

The composition of the present invention is a polyalkoxy fatty compound having the structure (I)

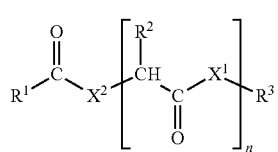

where $R^1$ is a fatty group; $R^2$ is H or a substituted or unsubstituted hydrocarbyl group; n is 0 to 5; $X^1$ is O, S, or NH; $X^2$ is O, S, or NH; and $R^3$ is a polymeric group comprising polymerized units of structure (II) and structure (III)

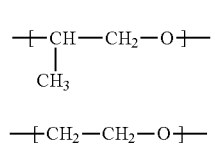

Preferably $R^1$ is a substituted or unsubstituted aliphatic group. Among substituted aliphatic groups, preferred substituent is hydroxyl. More preferably $R^1$ is an unsubstituted aliphatic group; more preferably, $R^1$ is an unsubstituted alkyl group. Preferably, $R^1$ is linear. Preferably, $R^1$ has 9 or more carbon atoms; more preferably 10 or more. Preferably, $R^1$ has 22 or fewer carbon atoms; more preferably 20 or fewer; more preferably 18 or fewer; more preferably 16 or fewer.

Preferably, $X^1$ is O or NH; more preferably NH. Preferably, $X^2$ is O or NH; more preferably NH.

Preferably, $R^2$ has 20 or fewer atoms; more preferably 15 or fewer. Preferably, if $R^2$ is not hydrogen, then $R^2$ contains one or more carbon atom. Preferably, $R^2$ is either hydrogen or an unsubstituted hydrocarbon group; more preferably, $R^2$ is either hydrogen, an unsubstituted alkyl group, or an alkyl group whose only substituent is an unsubstituted aromatic hydrocarbon group. Among unsubstituted alkyl groups, preferred is methyl. Among alkyl groups whose only substituent is an unsubstituted aromatic hydrocarbon group, preferred is —$CH_2$—($C_6H_5$), where —($C_6H_5$) is a benzene ring. Preferably, $R^2$ is chosen so that a compound with the structure (IV)

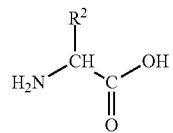

would be one of the 20 canonical biological amino acids.

Preferably, $R^3$ has number-average molecular weight of 600 or higher; more preferably 800 or higher. Preferably, $R^3$ has number-average molecular weight of 10,000 or less; more preferably 5,000 or less; more preferably 3,000 or less; more preferably 2,500 or less; more preferably 2,000 or less; more preferably 1,500 or less. Preferably, the group $R^3$ is either a statistical copolymer of (II) and (III) or a block copolymer of (II) and (III); more preferably the group $R^3$ is a statistical copolymer of (II) and (III). Preferably, —$R^3$ has the structure —$R^4$—$CH_3$, where $R^4$ is a polymeric group comprising polymerized units of structure (II) and structure (III). Preferably, $R^4$ has no other polymerized units in addition to structure (II) and (III).

Preferably, n is 0 or 1.

It is useful to characterize the mole ratio (herein the "PO/EO ratio") of units of structure (II) to units of structure (III). Preferably, the PO/EO ratio is 0.01:1 or greater; more preferably 0.02:1 or greater; more preferably 0.05:1 or greater; more preferably 0.1:1 or greater. Preferably, the PO/EO ratio is 2:1 or less; more preferably 1.5:1 or less; more preferably 1:1 or less; more preferably 0.5:1 or less.

Preferably, the compound of structure (I) has no ionic groups.

The compound of structure (I) may be made by any method. A preferred method is to react a compound having structure $NH_2$—$R^3$ with a compound selected from compounds of structure V

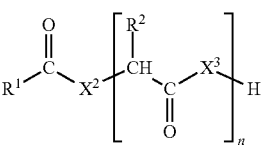

and compounds of structure VI

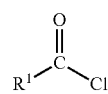

where $X^3$ is O, S, or NH. Preferences for $R^1$, $X^2$, $R^2$, $R^3$, and n are the same as those described above. Preferably, $X^3$ is O.

A more preferred method of making some embodiments of the compound of structure (I) is as follows. In a first step, an acyl chloride is reacted with an amino acid to form a carboxyl-functional fatty amide as follows:

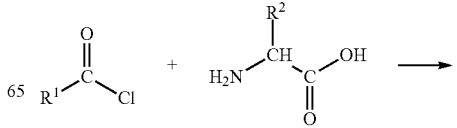

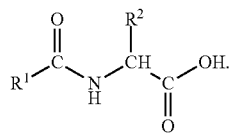

Then, in a second step, the carboxyl-functional fatty amide is reacted with an amine-terminated polyalkoxy compound, as follows:

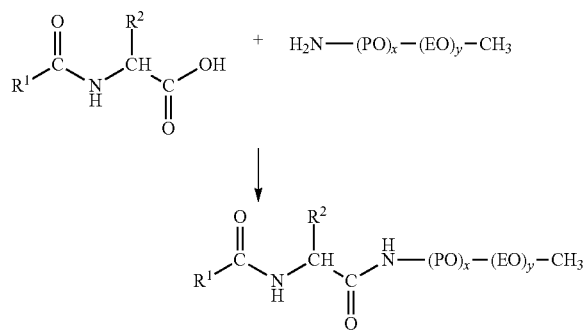

where PO is structure (II) and EO is structure (III).

A preferred use of the compound of structure (I) is in a composition that contains one or more protein and one or more compound of structure (I).

Preferred proteins have 40 or more polymerized units of amino acids; more preferably 100 or more.

Preferred proteins are selected from monoclonal antibodies, growth factors, insulins, immunoglobulins, polyclonal antibodies, hormones, enzymes, polypeptides, fusions of peptides, glycosylated proteins, antigens, antigen subunits, or combinations thereof. Preferred proteins have therapeutic efficacy to treat a disease or medical condition or to function as vaccines. Also contemplated are proteins that have a beneficial effect on a food composition or a cleaning composition or a coatings formulation.

Preferably, the weight ratio of protein to compound of structure (I) is 0.1:1 or greater; more preferably 0.2:1 or greater; more preferably 0.5:1 or greater; more preferably 0.9:1 or greater. Preferably, the weight ratio of protein to compound of structure (I) is 150:1 or less; more preferably 100:1 or less.

A preferred method of making a formulation that contains both a protein and a compound of structure (I) is to mix together water, one or more protein, one or more compound of structure (I), and optional additional ingredients to make a formulation (herein called formulation "F1") in which protein is dissolved in water.

Preferably, the amount of water in formulation F1, by weight based on the weight of formulation F1, is 50% or more; more preferably 60% or more; more preferably 70% or more.

In formulation F1, preferably the molecules of protein are not aggregated into large particles, even if the aggregated particles are dispersed in the liquid medium. Preferably, if any aggregated particles that contain protein molecules are present, the volume-average diameter of such particles is 10 nm or smaller; more preferably 6 nm or smaller.

In formulation F1, preferably the amount of protein is 0.01 mg/mL or more; more preferably 0.1 mg/mL or more; more preferably 0.9 mg/mL or more; In formulation F1, preferably the amount of protein is 400 mg/mL or less; more preferably 300 mg/mL or less; more preferably 250 mg/mL or less.

In formulation F1, preferably the amount of compound of structure (I) is 0.01 mg/mL or more; more preferably 0.1 mg/mL or more; more preferably 0.5 mg/mL or more. In formulation F1, preferably the amount of compound of structure (I) is 50 mg/mL or less; more preferably 10 mg/mL or less; more preferably 5 mg/mL or less.

Formulation F1 optionally contains one or more additional ingredients. Additional ingredients are compounds other than water, proteins, and compounds having structure (I). Preferred additional ingredients are surfactants not having structure (I), sugars, salts, buffers, amino acids, salts of amino acids, and mixtures thereof. When such additional ingredients are present, preferably the total amount of all additional ingredients is 300 mg/mL or less.

For inclusion in formulation F1, among surfactants not having structure (I), preferred are nonionic surfactants; more preferred are polyoxyethylene derivatives of sorbitan monolaurate (for example, polysorbate 20 and polysorbate 80) and triblock copolymers having a central block of polymerized units of propylene oxide and end blocks of polymerized units of ethylene oxide (for example polyoxamer F127 and polyoxamer 188).

For inclusion in formulation F1, preferred sugars are sucrose, glucose, mannose, trehalose, maltose, and mixtures thereof.

For inclusion in formulation F1, preferred salts have cations chosen from hydrogen, sodium, potassium, magnesium, calcium, ammonium, and mixtures thereof. Preferred salts have anions chosen from fluoride, chloride, bromide, iodide, phosphate, carbonate, acetate, citrate, sulfate, and mixtures thereof. Preferred buffers have cations chosen from hydrogen, sodium, potassium, magnesium, calcium, ammonium, and mixtures thereof. Preferred buffers have anions chosen from fluoride, chloride, bromide, iodide, phosphate, carbonate, acetate, citrate, sulfate, and mixtures thereof.

For inclusion in formulation F1, preferred amino acids and salts thereof are selected from lysine, glycine, arginine, histidine, and mixtures thereof.

In formulation F1, it is contemplated that the particles that contain protein are dissolved in a continuous aqueous medium. Of the compounds other than proteins that are present in formulation F1, each compound may, independently of the other compounds, be found dissolved in the aqueous medium; found in dispersed particles that do not contain protein; found attached to some or all of the dissolved molecules of protein; or found distributed between two or more of these locations.

It is contemplated that formulation F1 will have good stability. That is, it is contemplated that formulation F1 will resist denaturing of the protein and will resist agglomeration of the dissolved molecules into agglomerated particles.

One method of storing and/or transporting the mixture of protein and compound of structure (I) is to make a formulation F1 and then remove the water from formulation F1 through a drying process. It is contemplated that the solid material produced by drying formulation F1 (herein called solid "S") can be easily stored and transported without denaturing the protein or other degradation. It is further contemplated that, after transportation and/or storage, solid S1 can be mixed with water to produce a solution that has properties similar to the properties of formulation F1.

The following are examples of the present invention.

Procedures were conducted at room temperature, approximately 23° C., except where otherwise stated.

The following terms and abbreviations are used.

BSA=bovine serum albumin

IgG=immunoglobulin G; typically available from rabbit or human serum; in the examples below, the source of the IgG is noted.

THF=tetrahydrofuran

PO=structure (II)

EO=structure (III)

PEA1=Jeffamine™ M1000 polyetheramine (Hunstman), approximate molecular weight of 1,000, and PO/EO ratio of 3/19

PEA2=Jeffamine™ M2070 polyetheramine (Hunstman), approximate molecular weight of 2070, and PO/EO ratio of 10/31

Dynamic Light Scattering (DLS) measurements were performed as follows. Light scattering measurements were performed on a Wyatt DyanaPro™ high throughput DLS instrument. Samples were prepared with variable protein concentration and 1 mg/mL surfactant in citrate-saline buffer, pH 7, 15 millimolar sodium citrate, 150 millimolar sodium chloride. Orencia™ and Remicade™ powders were reconstituted with water rather than buffer. 30 µL of each sample were placed in the wells of an Aurora 384 well black cycloolefin polymer plate with clear bottom (Brooks Life Science Systems). On top of each well, 15 µL of silicone oil were added. For temperature ramp studies, the samples were allowed to equilibrate at 25° C. and then were ramped to 80° C. at 0.05 C/min. DLS measurements were obtained continuously, cycling from well to well with 5×3 sec acquisitions per well per cycle. For isothermal studies, the samples were ramped at 1° C./min to 40° C., 50° C., and the final temperature (50° C. for Remicade, 65° C. for BSA, 73° C. for Orencia) and data were collected continuously over approximately 36 hours.

The circular dichroism experiments (CD) were conducted on a JASCO J-1500 CD spectropolarimeter. Protein solutions [5% BSA (50 mg/mL), and 0.2% IgG (2 mg/mL)] were prepared in 10 mM phosphate buffered saline (PBS) buffer pH, 7.3. BSA samples were diluted 1:10 with PBS buffer before measurement.

Nano-Differential Scanning Calorimetry (nano-DSC) was performed using a Model 6100 Nano II DSC, Calorimetry Science Corporation, USA. Both the sample (typically 2.5 mg/ml protein solution) and the reference (phosphate buffer) were scanned at a pressure of 0.3 MPa (3 bars) and at 1° C./min scan rate. Scanning was from 15° C. to 105° C.

Synthesis of compound of structure (I) ("surfactant") was performed as follows:

N-myristoyl amino acid derivative was prepared by the reaction of myristoyl chloride with glycine in the presence of sodium hydroxide and triethylamine at room temperature (approximately 23° C.) for 4 hours. The N-myristoyl amino acid derivative (5 mmol) and polyetheramine (either PEA1 or PEA2) (5 mmol amine group) were added to a 50 mL one-neck round bottom flask containing a stir bar and fitted with a condenser and gas inlet adapter. The flask was placed into an oil bath and was heated as follows: 1 h at 100° C., 1 h at 125° C., 1 h at 150° C., 1.5 h at 175° C., and 1.5 h at 200° C. During this time, water evolution was observed once the reaction temperature reached 175-200° C. The reaction mixture was cooled to room temperature (approximately 23° C.), vacuum was applied to the flask, then the flask was reheated for 30 min at 100° C., 30 min at 125° C., 30 min at 150° C., 30 min at 175° C., and 2 h at 200° C. Heating was discontinued and the reaction mixture was allowed to cool to room temperature and then the flask was back-filled with nitrogen. 1H and 13C NMR spectra were consistent with the structures of the surfactants.

For compounds of structure (I) with n=0, the myristoyl chloride was reacted directly with the Jeffamine resin as described above.

In each inventive surfactant that was made, $R^1-$ was $CH_3(CH_2)_{11}CH_2-$. $X^1$ and $X^2$ were both N. $R^3$ was a copolymer of propylene oxide units and ethylene oxide units, end capped with a methyl group.

The inventive surfactants that were made were as follows:

| Example | Label | n | $R^2$ | PEA |
|---------|-------|---|-------|-----|
| 1 | GM1000 | 1 | H | PEA1 |
| 2 | AM1000 | 1 | $CH_3$ | PEA1 |
| 3 | FM1000 | 1 | note[(1)] | PEA1 |
| 4 | 0M1000 | 0 | none | PEA1 |
| 5 | GM2000 | 1 | H | PEA2 | note[(1)]:

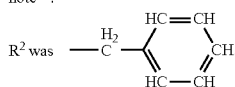

$R^2$ was

EXAMPLE 1

Testing of Protein Solutions Containing BSA

Scanning DLS of 5 mg/mL BSA with various surfactants as indicated. Scan speed was 0.05° C./min from 25 to 80° C. Surfactants were all 1 mg/mL. In scanning DLS, samples were tested for volume-average particle diameter as a function of temperature. Each sample eventually showed an increase in diameter. The temperature of the onset ($T_{onset}$) was recorded. Higher $T_{onset}$ means a more stable protein solution.

Nano-DSC of BSA (5 mg/mL) was performed with various surfactants (5 mg/mL). The Nano-DSC graph of heat flow vs. temperature shows a peak between 60° C. and 85° C. that is labeled the "unfolding" peak, and it indicates the temperature at which the protein denatures at maximal rate. The temperature of the unfolding peak (Tm) is reported. Higher Tm means a more stable the protein solution.

Circular dichroism (CD) BSA samples (5 mg/mL) with different surfactants were measured following heat aging at 70° C. for 30 minutes. The graph of CD vs. wavelength shows a peak at 222 nm, indicating absorbance of the alpha-helix. Decrease in the alpha-helix peak indicates denaturation. For each sample, the CD at 222 nm was examined, and the difference between the value of the initial sample was compared to the value of the same sample after heat aging at 70° C. for 30 minutes; this difference is reported as ΔCD. Higher absolute value of ΔCD means a less stable protein solution.

Also performed was isothermal DLS of BSA (5 mg/mL) with 1 mg/mL surfactants at 62° C. Volume-average particle diameter was measured as a function of time. The diameter at 2000 seconds (D2 k) was recorded. Lower value of D2 k means a more stable protein solution.

Results were as follows. "nt" means not tested.

| Type | Surfactant | $T_{onset}$ (° C.) | Tm (° C.) | ΔCD (mdeg) | D2k (nm) |
|------|-----------|--------------------|-----------|------------|----------|
| comparative | none | 57 | 61 | −30 | >100 |
| comparative | polysorbate 20 | 62 | 74 | −24 | 11 |
| comparative | polysorbate 80 | 60 | 74 | nt | 12 |
| comparative | n-dodecyl b-maltoside | 62 | nt | nt | 10 |

-continued

| Type | Surfactant | $T_{onset}$ (° C.) | Tm (° C.) | ΔCD (mdeg) | D2k (nm) |
|---|---|---|---|---|---|
| inventive | Example 3 | 70 | 76 | 3.9[(2)] | nt |
| inventive | Example 5 | 59 | nt | −18.7 | nt |
| inventive | Example 2 | 72 | 68 | −9.9 | nt |
| inventive | Example 4 | 75 | 84 | 0.5[(2)] | 6.5 |
| inventive | Example 1 | 64 | 73 | −10.8 | nt | note[(2)]:
values of 4 or less are considered to be equivalent to zero in view of experimental variability.

In the $T_{onset}$ results, all the inventive examples showed comparable or superior stability to the comparative examples, and Examples 2, 3, and 4 were especially superior to the comparative examples. In the Tm results, all the inventive examples showed comparable or superior stability to the comparative examples, and Example 4 was especially superior to the comparative examples. In the ΔCD results, all the inventive examples showed results far superior to the comparative samples. In the D2 k results, the only inventive example tested, Example 4, was superior to the comparative examples.

EXAMPLE 2

Testing of Protein Solutions Containing IgG

Scanning DLS was performed on protein solutions containing 1 mg/mL IgG from rabbit, at 0.05° C./min from 25° C. to 80° C., with surfactants all 1 mg/mL. $T_{onset}$ was 66° C. for all samples, but, as temperature was increased above $T_{onset}$, the sample using Example 1 showed much slower growth of particle diameter than all the other samples.

Isothermal DLS was performed at 1 mg/mL rabbit IgG at 65° C., and size at 4000 seconds (D4 k) was reported. CD technique using human IgG compared change in absorbance at 218 nm due to heat aging at 65° C. for 18 hours. Results were as follows:

| Type | Surfactant | D4k (nm) | ΔCD (mdeg) |
|---|---|---|---|
| comparative | none | >200 | −22 |
| comparative | polysorbate 20 | 22 | −21 |
| comparative | polysorbate 80 | 30 | nt |
| comparative | alkyl maltoside | 30 | nt |
| inventive | Example 3 | 12.2 | −15.5 |
| inventive | Example 5 | 40 | nt |
| inventive | Example 2 | 30 | −16 |
| inventive | Example 4 | 25 | −18 |
| inventive | Example 1 | 25 | −17.5 |

In the ΔCD results, the inventive examples were superior to the comparative examples. In the D4 k results, Example 3 was superior to the comparative examples.

EXAMPLE 3

Results using Orencia™ Powder

ORENCIA™ (abatacept) powder (manufactured by Bristol-Myers Squib) was obtained by prescription. Orencia was diluted with water to 4 mg/mL and tested by scanning DLS for $T_{onset}$. Also, Orencia was diluted to 10 mg/mL with water and tested by isothermal DLS at 73° C., and the diameter was noted at 20 hours (D20 h). In protein solutions, D20 h tends to grow larger as time passes, and less-stable solutions reach higher values of D20 h. Smaller value of D20 h means a more stable protein solution. Orencia solutions at 1 mg/mL were tested in an isothermal step experiment; particle diameter was measured by DLS as a function of time during a hold of 45 hours at 50° C., followed by 15 hours at 60° C. The diameter at the end of this process, Dstep, was recorded. Smaller values of Dstep means a more stable protein solution.

Results were as follows.

| Type | Surfactant | $T_{onset}$ (° C.) | D20 h (nm) | Dstep (nm) |
|---|---|---|---|---|
| comparative | none | 62 | >100 | >100 |
| comparative | polysorbate 20 | 62 | 6 | 5 |
| comparative | polysorbate 80 | 53 | 7 | 5.5 |
| comparative | poloxamer 188 | 70 | 6 | 5.1 |
| comparative | alkyl maltoside | 69 | 4.9 | 4.1 |
| inventive | Example 3 | >80 | 5.6 | 4.7 |
| inventive | Example 5 | 72 | 5.7 | 5.1 |
| inventive | Example 4 | 75 | 5.4 | 4.9 |

In the $T_{onset}$ and D20 h results, the inventive samples had more stable protein solutions than the comparative samples.

EXAMPLE 4

Test Results on Remicade™

REMICADE™ (infliximab) powder (manufactured by Johnson and Johnson) was obtained by prescription. Remicade powder was diluted to 1 mg/mL in water. Using scanning DLS, $T_{onset}$ was measured as described above. Also, isothermal DLS was performed at 50° C., and the time at which the particle diameter began to grow rapidly (t-grow) was noted. Results were as follows:

| Type | Surfactant | $T_{onset}$ (° C.) | t-grow (min) |
|---|---|---|---|
| comparative | none | 54 | <10 |
| comparative | polysorbate 20 | 53 | 1400 |
| comparative | polysorbate 80 | 54 | 1400 |
| comparative | alkyl maltoside | 53 | 625 |
| inventive | Example 3 | 53 | 535 |
| inventive | Example 5 | 53 | 1100 |
| inventive | Example 2 | 53 | 250 |
| inventive | Example 4 | 53 | 175 |
| inventive | Example 1 | 53 | 870 |

The inventive samples showed comparable performance to the comparative samples.

The invention claimed is:

1. A composition comprising water, one or more protein, and one or more polyalkoxy fatty compound that has structure (I)

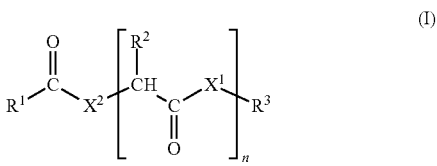

wherein $R^1$ is a fatty group; $R^2$ is H or a substituted or unsubstituted hydrocarbyl group; n is 0 to 5; $X^1$ is O, S, or NH; $X^2$ is O, S, or NH; $R^3$ has the structure $R^4$—$CH_3$, where $R^4$ is a polymeric group consisting of polymerized units of (II) and (III); and $R^3$ has number-average molecular weight of 600 or higher

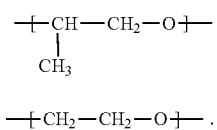

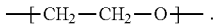

2. The composition of claim 1, wherein the polyalkoxy fatty compound is present in an amount of 0.01 mg/mL or more.

3. The composition of claim 1, wherein the protein is present in an amount of 400 mg/mL or less.

4. The composition of claim 1, wherein the water is present in an amount of 50% or more, by weight based on the weight of said composition, wherein said protein and said polyalkoxy fatty compound are dissolved or dispersed in said water.

5. The composition of claim 1, wherein the water is present in an amount of 50% or more, by weight based on the weight of said composition, wherein said protein and said polyalkoxy fatty compound are dissolved in said water.

6. The composition of claim 1, wherein said composition further comprises one or more additional ingredients, wherein the total amount of all additional ingredients is 300 mg/mL or less.

7. The composition of claim 1, wherein said protein is selected from monoclonal antibodies, growth factors, insulins, immunoglobulins, polyclonal antibodies, hormones, enzymes, polypeptides, fusions of peptides, glycosylated proteins, antigens, antigen subunits, and combinations thereof.

8. The composition of claim 1,
wherein —$R^1$ is a linear unsubstituted alkyl group having 10 to 16 carbon atoms,
wherein —$R^2$ is selected from the group consisting of hydrogen, methyl, and —$CH_2$—$(C_6H_5)$,
wherein —$(C_6H_5)$ is a benzene ring, and
wherein —$R^3$ has number-average molecular weight from 800 to 3000.

9. The composition of claim 1, wherein $X^2$ is NH.

10. The composition of claim 1, wherein n is 0 or 1.

11. The composition of claim 1, wherein $X^1$ is NH.

12. A composition comprising water, one or more protein, and one or more polyalkoxy fatty compound that has structure (I)

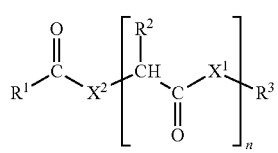

wherein $R^1$ is a fatty group; $R^2$ is H or a substituted or unsubstituted hydrocarbyl group; n is 1 to 5; $X^1$ is O, S, or NH; $X^2$ is O, S, or NH; and $R^3$ is a polymeric group comprising polymerized units of (II) and (III)

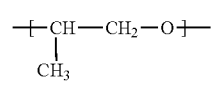

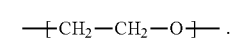

13. The composition of claim 12, wherein the polyalkoxy fatty compound is present in an amount of 0.01 mg/mL or more.

14. The composition of claim 12, wherein the protein is present in an amount of 400 mg/mL or less.

15. The composition of claim 12, wherein the water is present in an amount of 50% or more, by weight based on the weight of said composition, wherein said protein and said polyalkoxy fatty compound are dissolved or dispersed in said water.

16. The composition of claim 12, wherein the water is present in an amount of 50% or more, by weight based on the weight of said composition, wherein said protein and said polyalkoxy fatty compound are dissolved in said water.

17. The composition of claim 12, wherein said composition further comprises one or more additional ingredients, wherein the total amount of all additional ingredients is 300 mg/mL or less.

18. The composition of claim 12, wherein said protein is selected from monoclonal antibodies, growth factors, insulins, immunoglobulins, polyclonal antibodies, hormones, enzymes, polypeptides, fusions of peptides, glycosylated proteins, antigens, antigen subunits, and combinations thereof.

19. The composition of claim 12,
wherein —$R^1$ is a linear unsubstituted alkyl group having 10 to 16 carbon atoms,
wherein —$R^2$ is selected from the group consisting of hydrogen, methyl, and —$CH_2$—$(C_6H_5)$,
wherein —$(C_6H_5)$ is a benzene ring, and
wherein —$R^3$ has number-average molecular weight from 800 to 3000.

20. The composition of claim 12, wherein $X^2$ is NH.

21. The composition of claim 12, wherein n is 1.

22. The composition of claim 12, wherein $X^1$ is NH.

\* \* \* \* \*